United States Patent
Kirsch

(10) Patent No.: US 10,610,416 B2
(45) Date of Patent: Apr. 7, 2020

(54) SYSTEM, METHOD, AND PRODUCT FOR AN ADHESIVE STRIP CONFIGURED TO SELECTIVELY DISPENSE A FLUID

(71) Applicant: Adam A. Kirsch, Newbury, OH (US)

(72) Inventor: Adam A. Kirsch, Newbury, OH (US)

(73) Assignee: Adaco Innovations, LLC, Newbury, OH (US)

( * ) Notice: Subject to any disclaimer, the term of this patent is extended or adjusted under 35 U.S.C. 154(b) by 350 days.

(21) Appl. No.: 14/786,457

(22) PCT Filed: Mar. 14, 2014

(86) PCT No.: PCT/US2014/027563
§ 371 (c)(1),
(2) Date: Oct. 22, 2015

(87) PCT Pub. No.: WO2014/152639
PCT Pub. Date: Sep. 25, 2014

(65) Prior Publication Data
US 2016/0067105 A1     Mar. 10, 2016

Related U.S. Application Data

(60) Provisional application No. 61/787,671, filed on Mar. 15, 2013.

(51) Int. Cl.
*A61F 13/02*        (2006.01)
(52) U.S. Cl.
CPC ...... *A61F 13/0203* (2013.01); *A61F 13/0226* (2013.01); *A61F 13/0246* (2013.01)
(58) Field of Classification Search
CPC .............. A61F 13/0203; A61F 13/0226; A61F 13/0246
See application file for complete search history.

(56) References Cited

U.S. PATENT DOCUMENTS 4,117,841 A * 10/1978 Perrotta .............. A61F 13/0206
                                                    401/132
4,430,013 A    2/1984 Kaufman
(Continued)

OTHER PUBLICATIONS

International Search Report, Int'l filing date: Mar. 14, 2014, PCT/US14/27563, dated Aug. 18, 2014.
(Continued)

*Primary Examiner* — Tatyana Zalukaeva
*Assistant Examiner* — Jessica R Arble
(74) *Attorney, Agent, or Firm* — Benesch, Friedlander, Coplan & Aronoff LLP

(57) ABSTRACT

A fluid dispensing adhesive strip is presented. The fluid dispensing adhesive strip includes a backing layer having a first side and a second side, an adhesive that is disposed on at least a portion of the second side of the backing layer, and a packet that is disposed on the backing layer that includes a dispensable fluid and an activation mechanism that permits selective dispensing of the dispensable fluid. The packet can include multiple chambers configured to contain the same or different fluids, and channels associated with the chambers for dispensing the fluid when the activation mechanism is activated. The activation mechanism can be a tear-away strip, and can include perforations, serrations, and scoring to facilitate activation. Release strips in communication with the adhesive can releasably detach from the adhesive enabling the fluid dispensing strip to be applied and secured to an object or person.

15 Claims, 7 Drawing Sheets

(56) References Cited

U.S. PATENT DOCUMENTS

| | | | |
|---|---|---|---|
| 4,762,124 A | 8/1988 | Kerch et al. | |
| 5,326,685 A | 7/1994 | Gaglio et al. | |
| 5,756,117 A | 5/1998 | D'Angelo et al. | |
| 6,383,502 B1* | 5/2002 | Dunshee | A61K 8/31 |
| | | | 424/401 |
| 2006/0024358 A1 | 2/2006 | Santini, Jr. et al. | |
| 2008/0167633 A1* | 7/2008 | Vannucci | A61F 13/0203 |
| | | | 604/306 |
| 2009/0169137 A1* | 7/2009 | Allerup | A61F 15/001 |
| | | | 383/200 |
| 2012/0102885 A1* | 5/2012 | Sharp | B65B 61/202 |
| | | | 53/452 |
| 2013/0060184 A1* | 3/2013 | Rea | A61F 13/0246 |
| | | | 602/54 |
| 2013/0160408 A1* | 6/2013 | Neff | B65D 75/323 |
| | | | 53/492 |
| 2013/0245526 A1* | 9/2013 | Marascalco | A61L 15/28 |
| | | | 602/43 |

OTHER PUBLICATIONS

"TRG Reality: Medical Mutual Ads for Cleveland Browns", Published on Feb. 2, 2012, pp. 1-3.

* cited by examiner

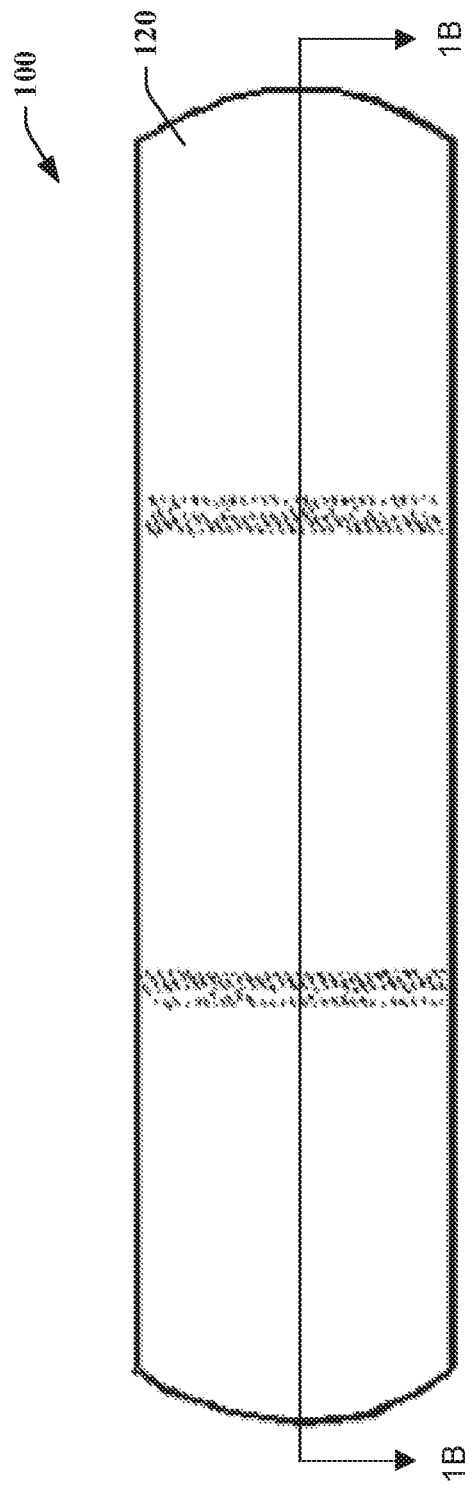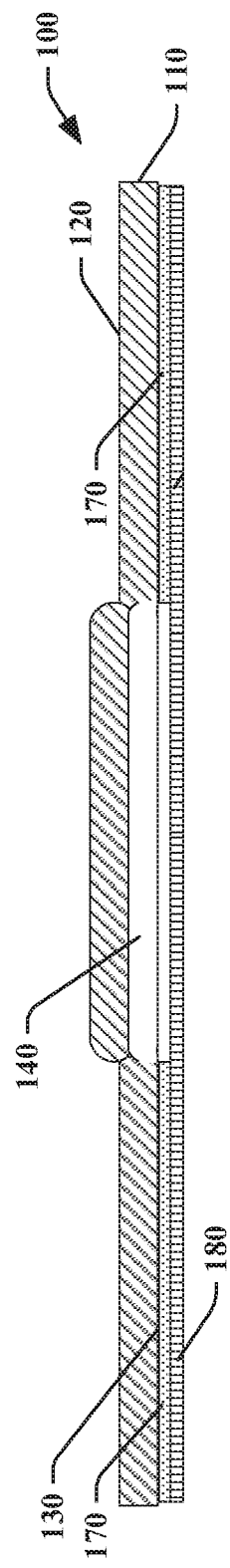

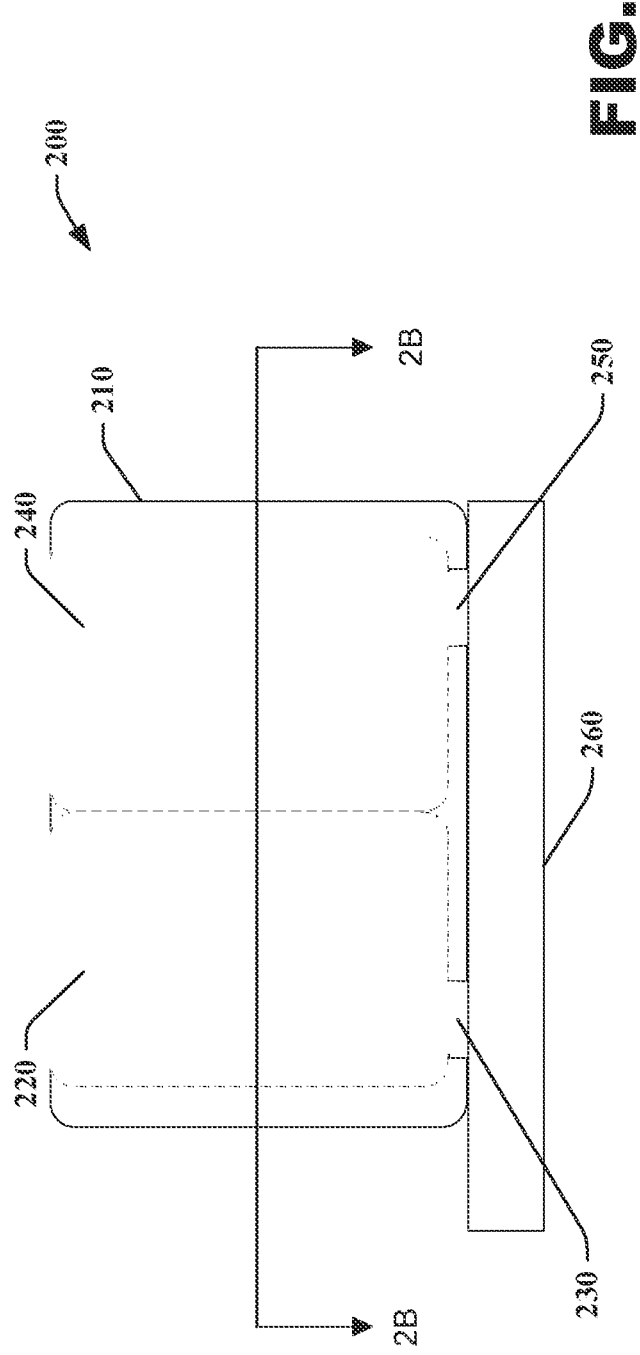
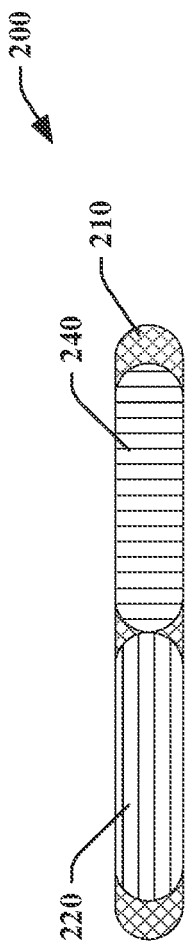
FIG. 2A
FIG. 2B

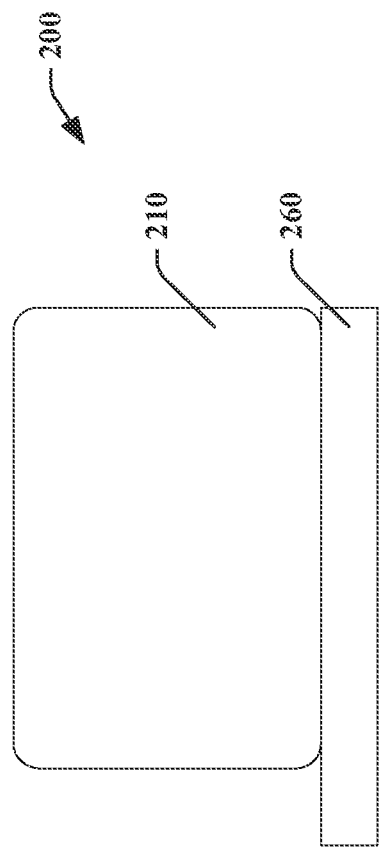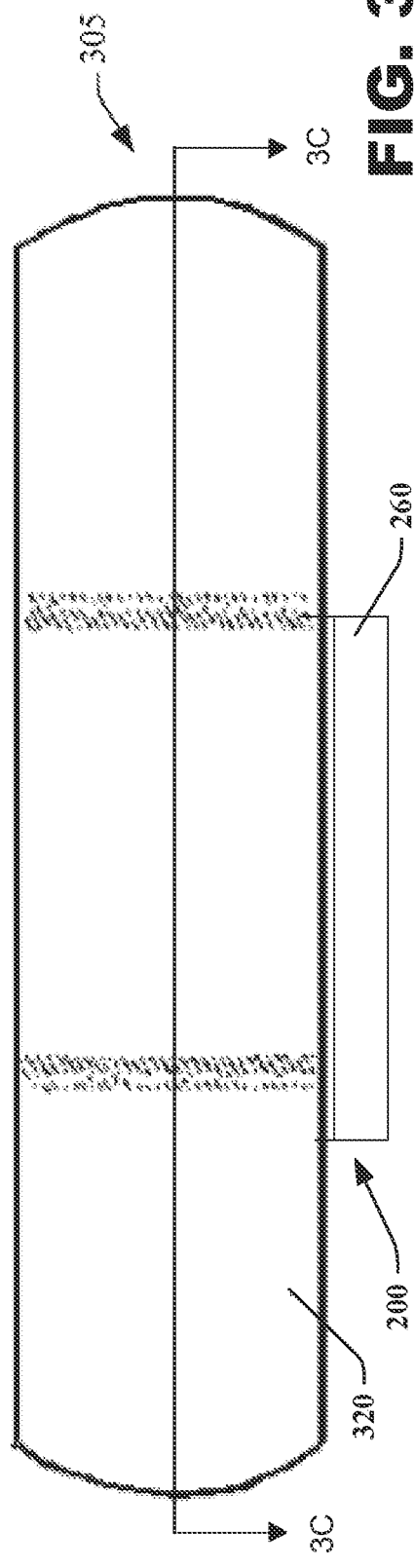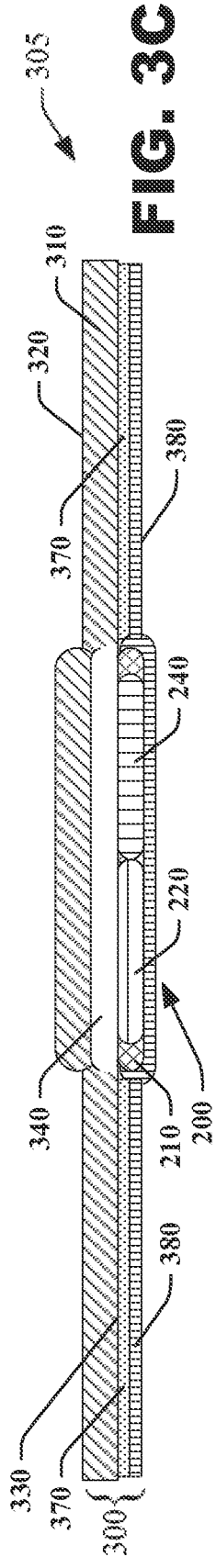

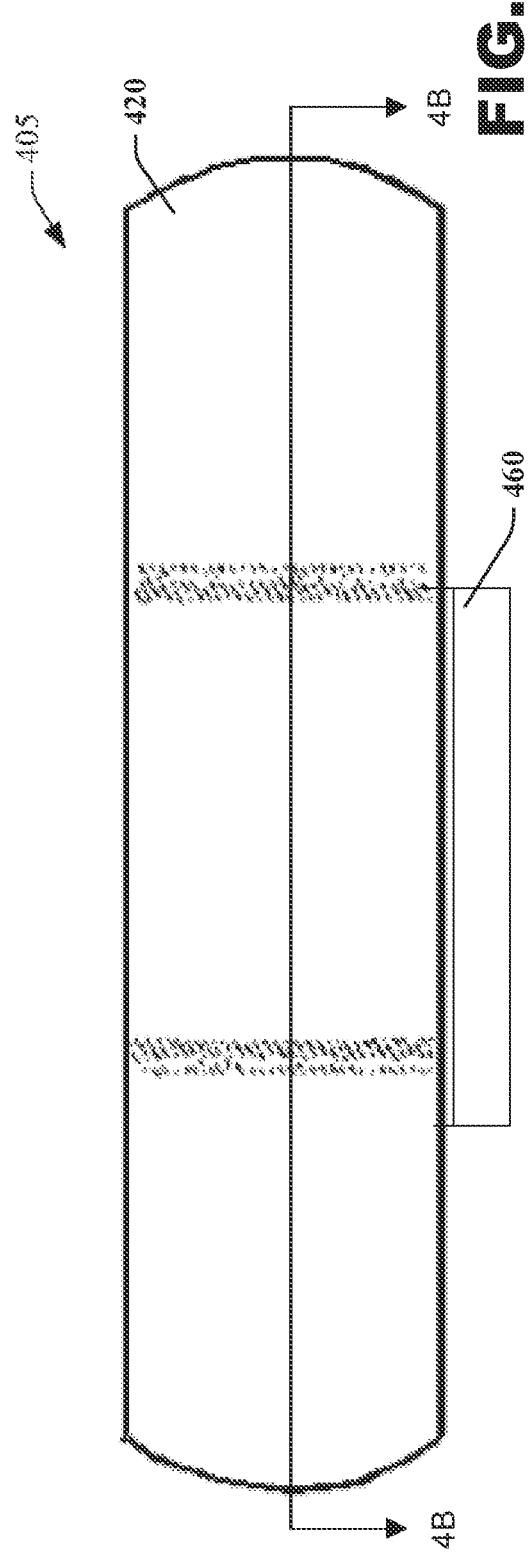
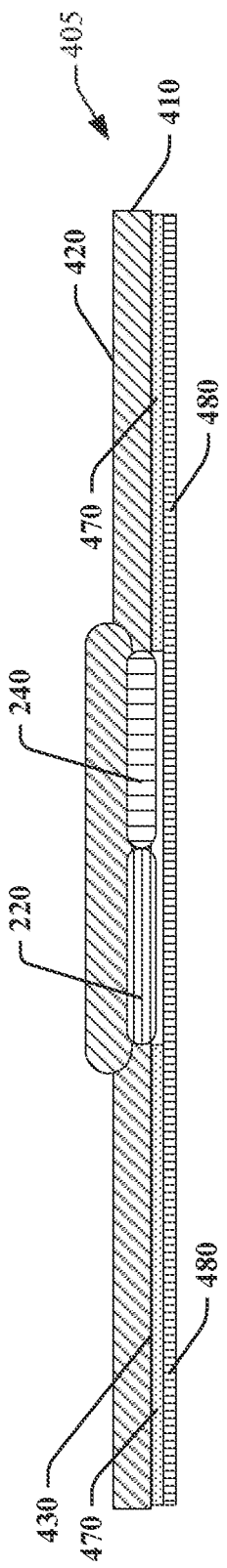

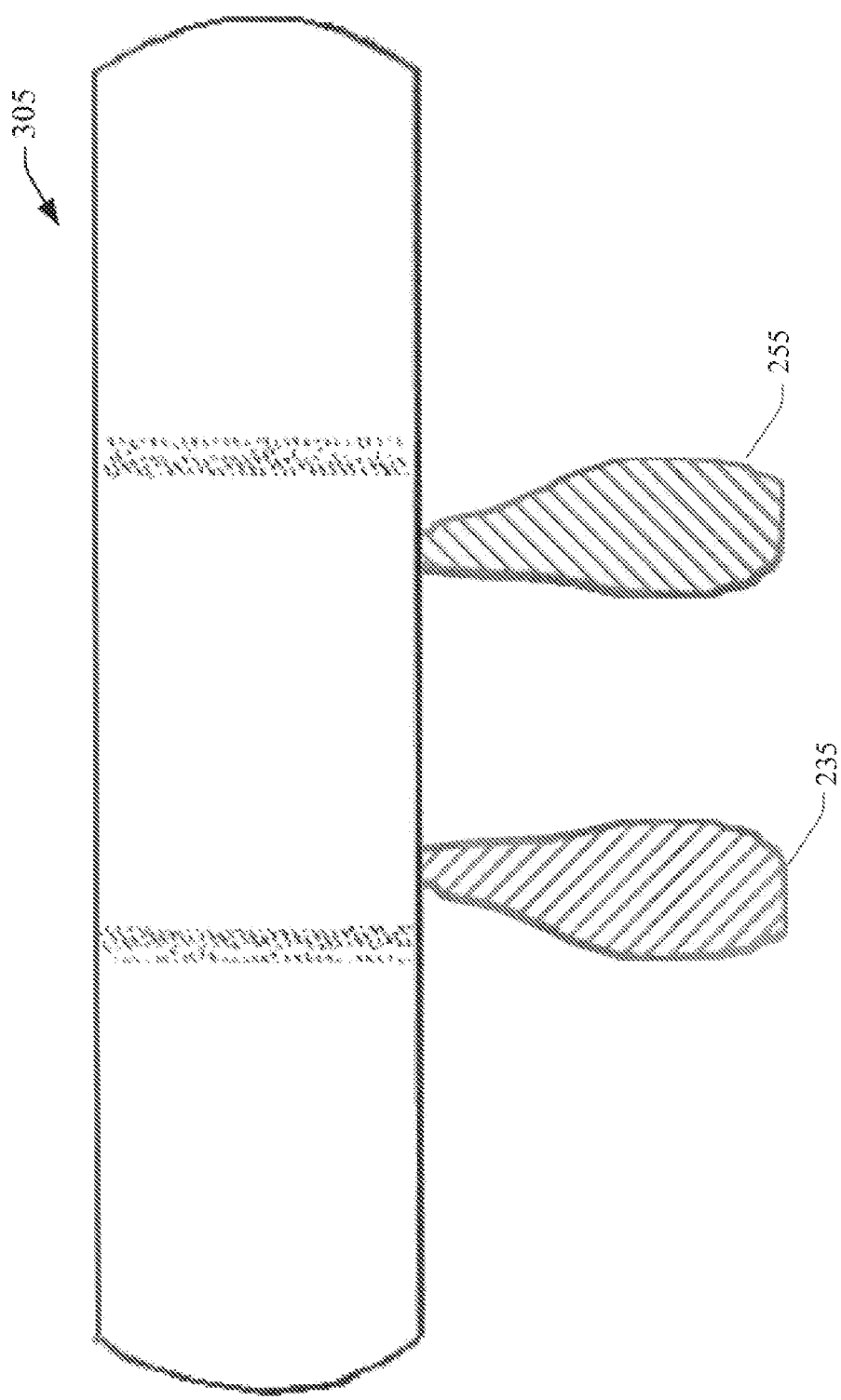

SYSTEM, METHOD, AND PRODUCT FOR AN ADHESIVE STRIP CONFIGURED TO SELECTIVELY DISPENSE A FLUID

REFERENCE TO RELATED APPLICATIONS

This application claims priority to U.S. Provisional Patent Application No. 61/787,671 filed Mar. 15, 2013, which is hereby incorporated herein by reference in its entirety.

TECHNICAL FIELD

The system, method and product described below relate generally to the field of dispensing one or more fluids from an adhesive strip, and more specifically, to the field of selectively dispensing colored fluid from fluid-filled packets attached to an adhesive strip for entertainment purposes.

SUMMARY

In accordance with one embodiment, an apparatus includes a backing layer having a first side and a second side, an adhesive disposed on at least a portion of the second side of the backing layer, and a packet disposed on the second side of the backing layer. The packet can include a fluid for dispensing and an activation mechanism that is configured to selectively allow dispensing of the fluid. The packet can further include one or more chambers, each of which is configured to contain the fluid, and one or more channels associated with the chambers, each of which is configured to dispense the fluid when the activation mechanism is activated. A plurality of chambers can be configured to hold a plurality of fluids and the channels can be configured to dispense the plurality of fluids when the activation mechanism is activated. The activation mechanism can be a tear-away strip, a perforated portion of the packet, a serrated portion of the packet, or a scored portion of the packet that is operably engaged with one or more of the channels through which the fluid can dispense. The apparatus can further include a protective portion, such as a pad, that is in communication with the second side of the backing layer. The apparatus can also include one or more release strips that are in communication with the adhesive and which can be configured to releasably detach from the adhesive. The adhesive can also be in communication with at least part of the packet and the release strips can be configured to releasably detach from the adhesive associated with the backing layer and the packet. The first side of the backing layer can be configured to accept markings such as a solid color, a translucent color, a plurality of colors, a pattern, a grid pattern, a perforation pattern, alphanumeric characters, a picture, a symbol, a graphic, a logo, a team logo, and a mascot. The fluid can be a paint, a non-toxic paint, a non-staining fluid, a dye, an ink, a colorant, and a colored liquid. The backing layer can be made of one or more materials such a polymeric material, polyethylene, polyurethane, polyvinyl chloride, plasticized polyvinyl chloride, a foam material, plastic foam, a fabric, woven fabric, knitted fabric, a clear material, a translucent material, and an opaque material.

In accordance with another embodiment, a method of dispending fluid from an adhesive strip can include removing release strips from the adhesive strip, applying the adhesive strip to an object or person, and activating the activation mechanism to dispense the fluid from a chamber of the adhesive strip. The adhesive strip can include a backing layer, a chamber in communication with the backing layer that contains the dispensable fluid, an activation mechanism configured to selectively dispense the dispensable fluid, and release strips operably coupled with at least the backing layer. The adhesive strip can further include a channel associated with the chamber that is opened at one end when activating the activation mechanism, and the method can further include dispensing the dispensable fluid from the chamber through the channel and out of the adhesive strip. The method can further include applying pressure to the chamber to dispense the dispensable fluid from the adhesive strip. The activation mechanism can be a tear-away strip, a perforation associated with the channel, and a scored end of the channel through which the dispensable fluid dispenses.

In accordance with another embodiment, a fluid dispensing adhesive strip can include an adhesive strip, one or more chambers in communication with the adhesive strip that are configured to dispense one or more fluids from the fluid dispensing adhesive strip when one or more tear strips are removed. The fluid dispensing adhesive strip can include one or more channels associated with the chambers that are configured to dispense the one or more fluids when one or more of the tear strips is removed. The fluid dispensing adhesive strip can also include one or more markings on the fluid dispensing adhesive strip including a solid color, a transparent color, a plurality of colors, a pattern, a grid pattern, a perforation pattern, one or more alphanumeric characters, a picture, a symbol, a graphic, a logo, a team logo, and a mascot. The backing layer of the fluid dispensing adhesive strip can be one or more materials such as a polymeric material, polyethylene, polyurethane, polyvinyl chloride, plasticized polyvinyl chloride, a foam material, plastic foam, a fabric, woven fabric, knitted fabric, a clear material, a translucent material, and an opaque material. The one or more fluids can each be a paint, a non-toxic paint, a non-staining fluid, a dye, an ink, a colorant, or a colored liquid. The fluid dispensing adhesive strip can include a pressure sensitive adhesive such as an acrylate adhesive or a hypoallergenic adhesive.

BRIEF DESCRIPTION OF THE DRAWINGS

FIG. 1A is a top plan view depicting a conventional adhesive bandage.

FIG. 1B is a cross-sectional view taken along line 1B-1B of FIG. 1A.

FIG. 2A is a top plan view depicting a fluid-dispensing packet with phantom lines outlining the position of interior chambers according to one embodiment.

FIG. 2B is a cross-sectional view taken along line 2B-2B of FIG. 2A.

FIG. 3A is a top plan view of the fluid-dispensing packet of FIG. 2A, without the chambers outlined.

FIG. 3B is a top plan view of a fluid-dispensing adhesive strip system according to one embodiment.

FIG. 3C is a cross-sectional view taken along line 3C-3C of FIG. 3B.

FIG. 4A depicts a top plan view depicting an alternative configuration of a fluid-dispensing adhesive strip.

FIG. 4B depicts a cross-sectional view taken along line 4B-4B of FIG. 4A.

FIG. 5 depicts a top view of the fluid-dispensing adhesive strip system of FIG. 3B, with the strip system in an activated configuration.

DETAILED DESCRIPTION

Figure 6:
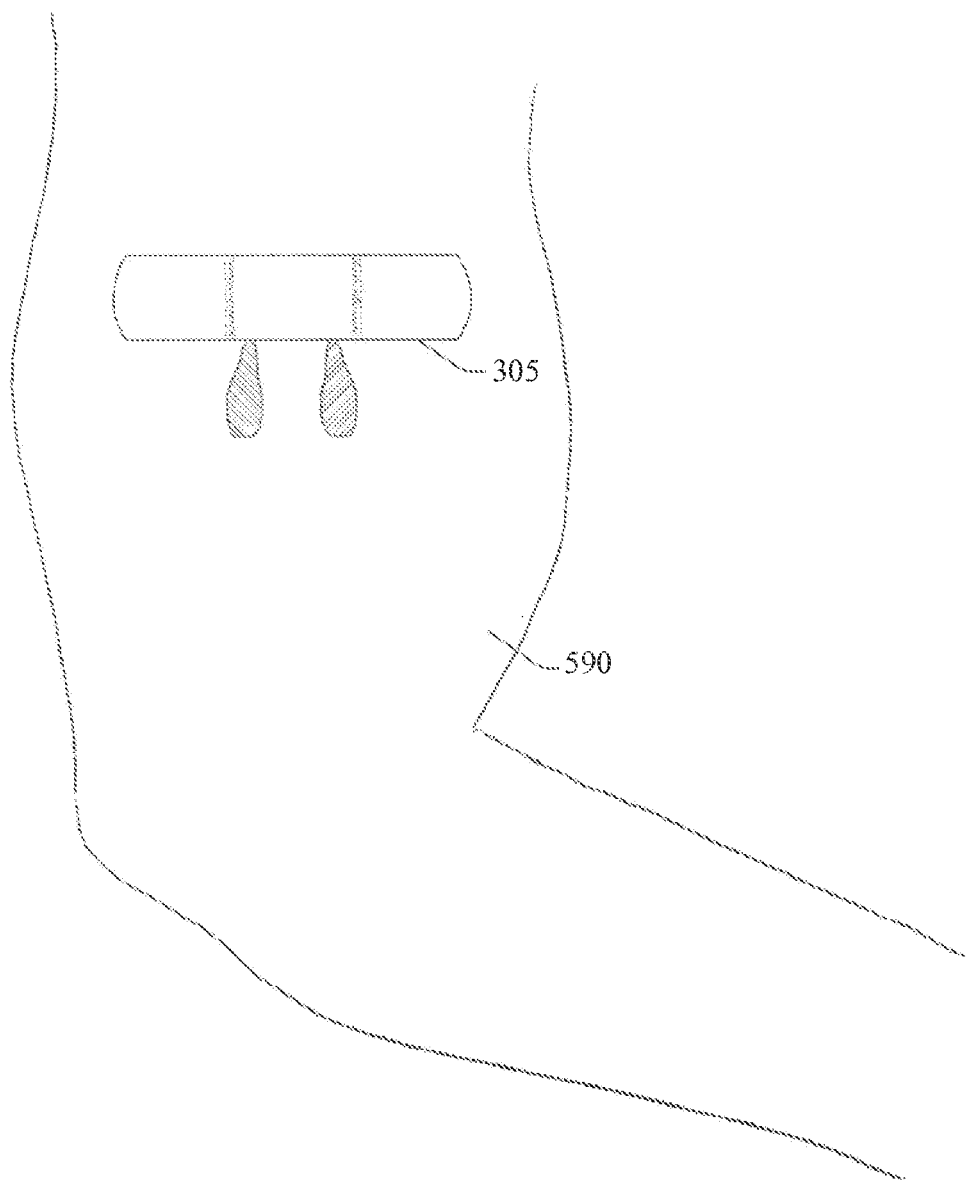
FIG. 6 depicts a top view of the activated fluid-dispensing adhesive strip system of FIG. 3B applied and dispensing fluids to a wearer's arm.

The systems, methods and products disclosed herein relate to an adhesive strip configured to selectively dispense fluids, and more specifically, to dispense one or more different colored fluids for entertainment purposes. An example entertainment purpose can include simulating the effect that the wearer is "bleeding" different colors. Applying and activating the disclosed fluid-dispensing adhesive strip on the wearer's skin can demonstrate team support and allegiance by "bleeding" the hallmark colors representative of a fan's favorite sports team.

Description of various components and methods are disclosed and described in detail with reference made to FIGS. 2A, 2B, 3A, 3B, 3C, 4A, 4B, and 5-7. The examples discussed below are examples only. They are provided to assist in the explanation of the disclosed systems, methods and products and illustrate specific examples and describe certain ways of making and using the disclosed systems, methods and products. None of the features or components shown in the drawings or discussed should be interpreted as mandatory or limiting for any specific implementation unless specifically designated as such. Conversely, the features and components shown in the drawings are not intended to disclose, and should not be taken as an exhaustive list, of all the possible implementations of the disclosed systems, methods and products.

For ease of reading and clarity, certain materials or methods may be described solely in connection with a specific figure. Like reference numerals are generally intended to refer to the same or similar materials.

Turning to the figures, a conventional adhesive bandage 100 is shown in FIGS. 1A and 1B. The bandage 100 generally includes a backing layer 110, for example a polymeric backing layer, with a first side 120 and a second side 130. As is known to those of skill in the art, the backing layer 110 may be formed from a polymeric material such as plastic film polyethylene, polyurethane, polyvinyl chloride, or plasticized polyvinyl chloride), plastic foam, woven or knitted fabric, non-woven fabric or other suitable material configured to accommodate a wearer's movement and adjust to the shape of his or her body. The backing layer 110 may be clear, translucent or opaque and may be perforated in a grid or other pattern (not shown).

As is more clearly shown in FIG. 1B, a protective or absorbent portion 140 (e.g. a gauze pad), is typically attached to the central region of the first side 130 of the backing layer 110. The absorbent portion 140 is constructed of material known in the art, such as rayon fibers, polyester fibers or a blend of such fibers. Other fibers, e.g., cotton fibers or polyolefin fibers may also be used in constructing the absorbent on 140. The absorbent portion 140 is attached to the backing layer 110 by hot melt glue or another conventional strong glue.

The backing layer 110 extends in opposite directions from the absorbent portion 140 and includes a coating of pressure sensitive adhesive 170 on the second side 130 that permits attachment of the bandage 100 to a wearer's skin. As shown, pressure sensitive adhesive 170 may not be included in the location of the absorbent portion 140. The pressure sensitive adhesive 170 can be, for example an acrylate adhesive or other suitable adhesive conventionally used for bandages as is known by those of skill in the art. The pressure sensitive adhesive 170 is typically hypoallergenic so as to be capable of contacting the wearer's skin for a prolonged period of time without causing irritation. The pressure sensitive adhesive 170 can also be sufficiently strong to retain the bandage 100 securely against skin but can be flexible to also allow movement of the skin.

Conventional bandages 100 also generally include at least one release strip 180, as shown in FIG. 1B, and typically include two release strips in overlapping relation (not shown). The release strip 180 may be made from any suitable material such as paper having a silicone release material coated thereon, or a low surface energy plastic film such as polyethylene or polystyrene. The release strip 180 contacts the absorbent portion 140 and pressure sensitive adhesive layer 170. While the release strip 180 is in place, the bandage 100 is readily handled without difficulty, and the pressure sensitive adhesive 170 does not inadvertently become activated and unintentionally adhere to an object.

FIG. 2A shows an embodiment of a fluid-dispensing packet 200. The packet 200 can be made of any suitable material, including foil, plastic or polymeric material. The packet 200 can include a casing 210 and a fluid-dispensing activation mechanism 260. Casing 210 can define chambers 220 and 240 and channels 230 and 250. Phantom lines outline the position of chambers 220 and 240 in FIG. 2A. Chambers 220 and 240 can respectively be in fluid communication with channels 230 and 250. The activation mechanism 260 can be a tear-away strip that can be releasably attached to casing 210, however, other suitable means to open and allow the release of the fluid within casing 210 are contemplated. For example, in other embodiments the activation mechanism 260 can include a perforated or serrated portion. Likewise, a score line may be included to further define the channels 230 and 250 out of which the fluid or material can exit from the chambers 220 and 240 after tearing along the score line.

FIG. 2B is a horizontal cross-section of packet 200 and further illustrates chambers 220 and 240. Although two similarly sized and shaped chambers 220 and 240 are shown together, any suitable number of chambers 220 and 240 of identical or dissimilar sizes and shapes may be included. For example, packet 200 can include a single chamber, two chambers (as shown), or sufficient chambers for a particular purpose, for example sufficient chambers to produce a series of colored fluids when the fluids are dispensed. In one embodiment, the chambers 220 and 240 can be arranged in any suitable configuration, for example vertically or horizontally as shown. As will be recognized by one of skill in the art, casing 210 can be formed from individual sheet portions that can be bonded or sealed by thermal heat, microwaves, ultrasonic heating or another manner sufficient to affix the sheets together at an outer periphery and along an internal line to form chambers 220 and 240 of casing 210. Chambers 220 and 240 can also be formed by embossing casing 210. Alternatively, casing 210 may be formed from a single sheet which may be folded over upon itself to form two adjacent sheets or sheet portions and then further sealed or bonded to define chambers 220 and 240. Chambers 220 and 240 can be isolated from each other and ambient air, and can be filled, for example, with fluids by injection or by any other suitable method. It will be apparent to those skilled in the art that the method does not have to be performed in the explicit or implicit order presented but rather may be performed in a different order or in parallel.

Each of the chambers 220 and 240 can include a respective channel 230 and 250 for fluid exit, although more than one channel may be included per chamber. The channels 230 and 250 may be narrower than the width of the chambers 220 and 240 to assist in directing fluids once released. Alternatively, channels 230 and 250 may be as wide as the chambers 220 and 240 permit. Channels 230 and 250 can also be any suitable shape, including funnel-shaped. Channels 230 and 250 can extend through an outer periphery of the casing 210.

Chambers 220 and 240 can contain fluids, for example, paints, inks, dyes or colorants, which may be similar or dissimilar in color. In one embodiment, the fluids do not plasticize and do not cause the pressure sensitive adhesive 170 to lose its adherence or otherwise react with the pressure sensitive adhesive 170 to leave unwanted residue on the user's skin. Fluids can be, for example, non-toxic face or body paints commonly known in the art. Fluids can also be non-staining to clothing and household fabrics and capable of being removed with simple soap and water washing. In an example, chamber 220 contains red paint (see FIG. 5, red paint 235), and chamber 240 contains blue paint (see FIG. 5, blue paint 255).

FIG. 3A is a top plan view of the fluid-dispensing packet 200. However, FIG. 3A does not include phantom-outlined positions of chambers 220 and 240 shown in FIG. 2A.

FIG. 3B depicts the top view of a fluid dispensing adhesive strip system 305, which can include packet 200, activation mechanism 260 and adhesive strip 300 in relative positions.

FIG. 3C depicts a cross-sectional view of FIG. 3B along line 3C-3C. The cross-sectional view depicts a configuration of the fluid dispensing adhesive strip system 305. In FIG. 3C, adhesive strip 300 can be composed of backing layer 310, absorbent portion 340, pressure sensitive adhesive 370 and release strip. Backing layer 310 has a first side 320 that can be configured to accept a design, logo, or label. The backing layer 310 has a second side 330 that can be coated with a coating of pressure sensitive adhesive 370 that permits attachment of the fluid-dispensing adhesive strip system 305 to a wearer's skin. One or more release strips 380 can be configured in an overlapping relation. The packet 200 can be aligned with an absorbent portion 340. The fluid dispensing adhesive strip system 305 can attach to a wearer's skin as the placement of the packet 200 permits pressure sensitive adhesive 370 of adhesive strip 300 to contact and adhere to the wearer's skin. Packet 200 may also include adhesive, such as pressure sensitive adhesive, to adhere to the absorbent portion 340 as well as to adhere to the wearer's skin. Such adhesive can assist in maintaining the position of the packet 200 with respect to the adhesive strip 300, and the wearer's skin. FIG. 3C shows two separated chambers 220 and 240 which can contain colorants or colored liquids (see, for example, FIG. 5, red paint 235, and blue paint 255).

Referring now to FIGS. 4A and 4B, another embodiment of a fluid-dispensing adhesive strip system 405 is illustrated. Fluid-dispensing adhesive strip system 405 can include a backing layer 410, a backing layer first side 420, a backing layer second side 430, a fluid-dispensing activation mechanism 460, pressure sensitive adhesive 470 and a release strip 480. The fluid-dispensing adhesive strip system 405 lacks an absorbent portion such as 340 in adhesive strip 300 shown in FIG. 3C. Chambers 220 and 240 can be defined as a result of the integral construction of the fluid-dispensing adhesive strip system 405. Release of the colorants in chambers 220 and 240 can occur through the removal of the fluid-dispensing activation mechanism or tear-away strip 460.

FIG. 5 shows the system fluid-dispensing adhesive strip system 305 after activation. In use, a user separates and removes the release strip 380 from the pressure sensitive adhesive 370. The user then applies the fluid dispensing adhesive strip system 305 to a part of the skin and then gently applies pressure to the pressure sensitive adhesive 370 of the fluid dispensing adhesive strip system 305. This pressure activates the pressure sensitive adhesive 370 and secures the fluid dispensing adhesive strip system 305 to the skin. The user releases paints 235 and 255 from chambers 220 and 240 by removing the tear-away strip 260. Optionally, once the tear-away strip 260 is removed, the user may gently apply pressure to the fluid dispensing adhesive strip system 305 to dispense the paints 235 and 255 to flow down the wearer's body. Alternatively, packet 200 and adhesive strip 300 may be provided separately and assembled by a user for application and activation.

Figure 7:
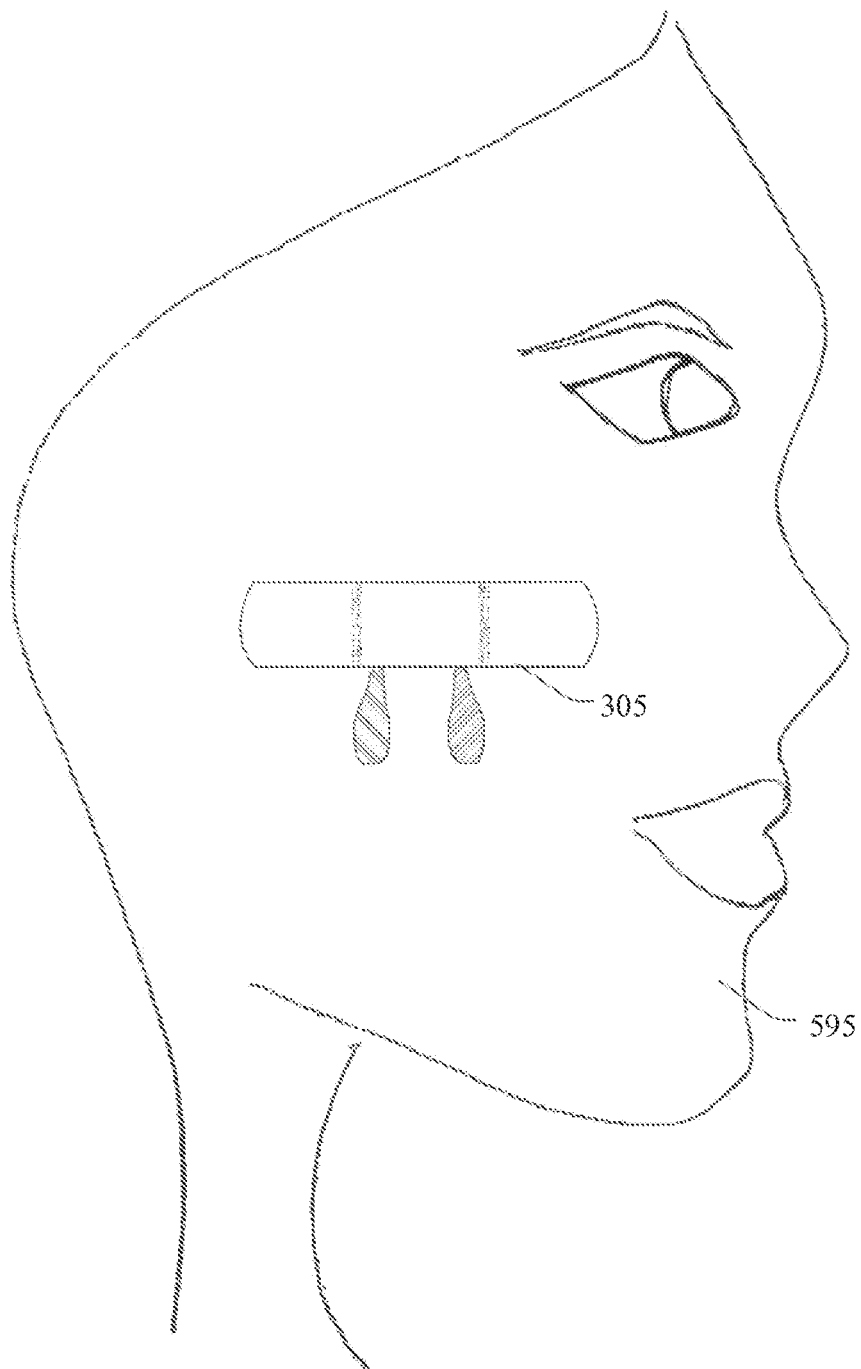
FIG. 7 depicts a top view of the activated fluid-dispensing adhesive strip system of FIG. 3B applied and dispensing fluids to a wearer's face.

FIGS. 6 and 7 depicts the activated fluid dispensing adhesive strip system 305 applied to a wearer's arm 590 and face 595, respectively. As such, fluid dispensing adhesive strip systems 305 and 405, packet 200 and adhesive strip 300 may be of shapes and sizes suitable for use on various surfaces or parts of the body, such as the arm 590 or face 595. Additionally, the first side 320 of the backing layer 310 may include alphanumeric text, colors, pictures, symbols, or graphics, such as a team logo and mascot, to further show team pride. Further, backing layer 310 may be embossed, for example, with a grid of dots to connote the illusion or concept of a medical bandage. A picture may act as a visual guide as to either the color of the internal content or where the contents of the pouch will exit after the activation mechanism 260 is removed.

Although systems, methods and products described herein can be used to dispense fluids and simulate the effect of the wearer "bleeding" his or her team colors, those of ordinary skill in the art will recognize that any other suitable means for making an adhesive strip configured to selectively dispense fluids can be used. Modifications to the disclosed products and methods can and may be made for a specific application. Such modifications may include substitutions of materials, changes to the types and shapes of the fluid-dispensing adhesive strips, and other arrangements of layers of plastic, woven fabric, or porous-polymer coatings. Modifications may also be made between or among examples and among combinations of materials. Failure to explicitly describe a combination or sub-combination of materials should not be understood to indicate that the combination or sub-combination is not possible. Such modifications and variations should be apparent to those of ordinary skill in the area after having read this document.

What is claimed is:

1. A fluid-dispensing adhesive strip for adherence to skin, comprising:
 a backing layer having a first side and a second side;
 an adhesive capable of adhering to skin disposed on at least a portion of the second side of the backing layer;
 a packet disposed on the second side of the backing layer comprising a first chamber and a second chamber,
  wherein the first chamber contains a first decorative paint, dye, ink, colorant, or colored liquid,
  wherein the second chamber contains a second decorative paint, dye, ink, colorant, or colored liquid, and
  wherein the first decorative paint, dye, ink, colorant, or colored liquid, and the second decorative paint, dye, ink, colorant, or colored liquid are different colors; and
 a means for releasing the first decorative paint, dye, ink, colorant, or colored liquid and the second decorative paint, dye, ink, colorant, or colored liquid from the packet such that the first decorative paint, dye, ink, colorant, or colored liquid and the second decorative paint, dye, ink, colorant, or colored liquid flows outwardly from the packet and away from the adhesive strip along the skin while the adhesive is adhered to the skin.

2. The fluid-dispensing adhesive strip of claim 1, wherein the packet further includes:
a channel associated with each of the first chamber and the second chamber such that upon releasing, the first decorative paint, dye, ink, colorant, or colored liquid and the second decorative paint, dye, ink, colorant, or colored liquid flow from the first chamber and the second chamber through the channel of each of the first chamber and the second chamber and out of the packet.

3. The fluid-dispensing adhesive strip of claim 1, wherein the means for releasing the first decorative paint, dye, ink, colorant, or colored liquid and the second decorative paint, dye, ink, colorant, or colored liquid is one of a tear-away strip, a perforated portion of the packet, a serrated portion of the packet, or a scored portion of the packet.

4. The fluid-dispensing adhesive strip of claim 1, further comprising:
a protective portion in communication with the second side of the backing layer.

5. The fluid-dispensing adhesive strip of claim 1, further comprising:
at least one release strip in communication with the adhesive, and wherein the at least one release strip is configured to releasably detach from the adhesive.

6. The fluid-dispensing adhesive strip of claim 5, wherein the adhesive is also in communication with at least a portion of the packet, and wherein the at least one release strip is configured to releasably detach from the adhesive associated with the backing layer and the packet.

7. The fluid-dispensing adhesive strip of claim 1, wherein the first side of the backing layer is configured to accept at least one marking, and wherein each marking comprises a solid color, a translucent color, a plurality of colors, a pattern, a grid a perforation pattern, one or more alphanumeric characters, a picture, a symbol, a graphic, a logo, a team logo, or a mascot.

8. The fluid-dispensing adhesive strip of claim 1, wherein the first decorative paint, dye, ink, colorant, or colored liquid and the second decorative paint, dye, ink, colorant, or colored liquid are non-toxic and non-staining.

9. The fluid dispensing adhesive strip of claim 1, wherein the backing layer is a material selected from the group consisting of a polymeric material, polyethylene, polyurethane, polyvinyl chloride, plasticized polyvinyl chloride, a foam material, plastic foam, a fabric, a woven fabric, knitted fabric, a clear material, a translucent material, and an opaque material.

10. A fluid dispensing adhesive strip, comprising:
an adhesive strip;
a first chamber and a second chamber in communication with the adhesive strip,
wherein the first chamber contains a first decorative paint, dye, ink, colorant, or colored liquid,
wherein the second chamber contains a second decorative paint, dye, ink, colorant, or colored liquid, and
wherein the first decorative paint, dye, ink, colorant, or colored liquid and the second decorative paint, dye, ink, colorant, or colored liquid are different colors; and
at least one tear strip in removable communication with the first chamber and the second chamber such that removal of the at least one tear strip causes the first decorative paint, dye, ink, colorant, or colored liquid and the second decorative paint, dye, ink, colorant, or colored liquid to exit the first chamber and the second chamber and flow outwardly away from the adhesive strip along a skin while the adhesive is adhered to the skin.

11. The fluid dispensing adhesive strip of claim 10, further comprising:
a channel extending from each of the first chamber and the second chamber to the at least one tear strip, wherein removing the at least one tear strip causes the first decorative paint, dye, ink, colorant, or colored liquid and the second decorative paint, dye, ink, colorant, or colored liquid to flow from each of the first chamber and the second chamber through the channel of each of the first chamber and the second chamber and outwardly away from the adhesive strip.

12. The fluid dispensing adhesive strip of claim 10, further comprising: one or more markings on the fluid dispensing adhesive strip, wherein each marking is selected from the group consisting a solid color, a translucent color, a plurality of colors, a pattern, a grid a perforation pattern, one or more alphanumeric characters, a picture, a symbol, a graphic, a logo, a team logo, or a mascot.

13. The fluid dispensing adhesive strip of claim 10, further comprising a backing layer, wherein the backing layer is a material selected from the group consisting of a polymeric material, polyethylene, polyurethane, polyvinyl chloride, plasticized polyvinyl chloride, a foam material, plastic foam, a fabric, woven fabric, knitted fabric, a clear material, a translucent material, and an opaque material.

14. The fluid dispensing adhesive strip of claim 10, wherein the first decorative paint, dye, ink, colorant, or colored liquid and the second decorative paint, dye, ink, colorant, or colored liquid are non-toxic and non-staining.

15. The fluid dispensing adhesive strip of claim 10, wherein the adhesive strip includes a pressure sensitive adhesive selected from the group consisting of an acrylate adhesive, and a hypoallergenic adhesive.

* * * * *